(12) United States Patent
Turetsky et al.

(10) Patent No.: US 8,080,404 B1
(45) Date of Patent: Dec. 20, 2011

(54) ENZYMATIC DECONTAMINATION

(75) Inventors: Abraham L. Turetsky, Baltimore, MD (US); David R. Pawlowski, Bel Air, MD (US); Mark D. Brickhouse, Newark, DE (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/328,477

(22) Filed: Jan. 9, 2006

Related U.S. Application Data

(60) Provisional application No. 60/668,259, filed on Apr. 5, 2005.

(51) Int. Cl.
  *A62D 3/00* (2007.01)
  *A62D 3/02* (2007.01)
  *B09B 3/00* (2006.01)
  *B09C 1/10* (2006.01)
  *C02F 1/02* (2006.01)
  *C02F 3/00* (2006.01)
  *C02F 3/34* (2006.01)
  *C12N 9/02* (2006.01)
  *C12Q 1/26* (2006.01)

(52) U.S. Cl. .......... 435/262.5; 210/600; 210/606; 435/25; 435/189; 435/262; 435/832

(58) Field of Classification Search .............. None
See application file for complete search history.

(56) References Cited

U.S. PATENT DOCUMENTS

| | | | | |
|---|---|---|---|---|
| 2,843,545 A | * | 7/1958 | Wolf | 166/275 |
| 5,262,151 A | * | 11/1993 | Montgomery | 424/50 |
| 5,403,450 A | * | 4/1995 | Mellor et al. | 435/25 |
| 5,429,726 A | * | 7/1995 | Johnson et al. | 205/778 |
| 5,747,078 A | * | 5/1998 | De Jong et al. | 426/9 |
| 6,716,976 B1 | * | 4/2004 | Jetten et al. | 536/124 |
| 6,824,645 B2 | * | 11/2004 | Jaschinski et al. | 162/9 |
| 6,964,787 B2 | * | 11/2005 | Swart et al. | 426/234 |
| 7,005,294 B2 | * | 2/2006 | Lehmann | 435/287.8 |
| 7,033,781 B1 | * | 4/2006 | Short | 435/69.1 |
| 2003/0158459 A1 | * | 8/2003 | Tucker | 588/200 |
| 2003/0211005 A1 | * | 11/2003 | Sloan et al. | 422/20 |
| 2003/0211169 A1 | * | 11/2003 | Tabasso | 424/616 |
| 2004/0142338 A1 | * | 7/2004 | Lehmann | 435/6 |

FOREIGN PATENT DOCUMENTS

EP 518 445 A1 * 6/1992

* cited by examiner

*Primary Examiner* — Debbie K Ware
(74) *Attorney, Agent, or Firm* — Ulysses John Biffoni

(57) ABSTRACT

Compositions and methods for enzymatic decontamination by inactivation of Hazardous agents are provided. Hazardous agents of microbial and chemical origin can be neutralized by $H_2O_2$. The methods described herein provide for enzymatic production of $H_2O_2$ in situ using oxidoreductase enzymes that use oxygen as an acceptor and their alcohol substrates. The enzymatically produced $H_2O_2$ and corresponding aldehydes have potent antimicrobial properties. The enzymatically produced $H_2O_2$ also can detoxify chemical agents in situ. The decontaminating power of the oxidoreductase enzymes that use oxygen as an acceptor may be amplified by addition of reagents, such as acetyl donors or base catalysts that, in the presence of $H_2O_2$, yield peroxy acid derivatives and hydroperoxy anions. Such derivatives can neutralize biological and chemical agents, thus providing a broadly applicable decontamination method. In addition, catalytic production of $H_2O_2$ in situ results in controlled synthesis of decontamination reagents at their point of use, mitigating the need to store, transport and dispose of hydrogen peroxide solutions in the field.

22 Claims, 7 Drawing Sheets

ALCOHOL OXIDASE SUBSTRATE COMPARISON

SPORICIDAL ACTIVITY OF ALCOHOL OXIDASE IN 10% METHANOL

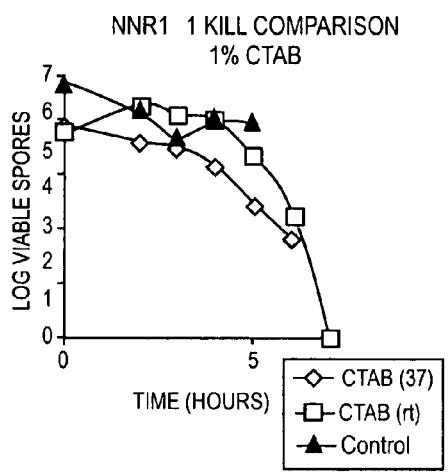
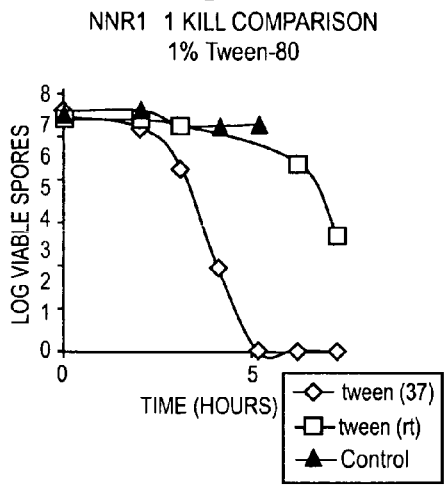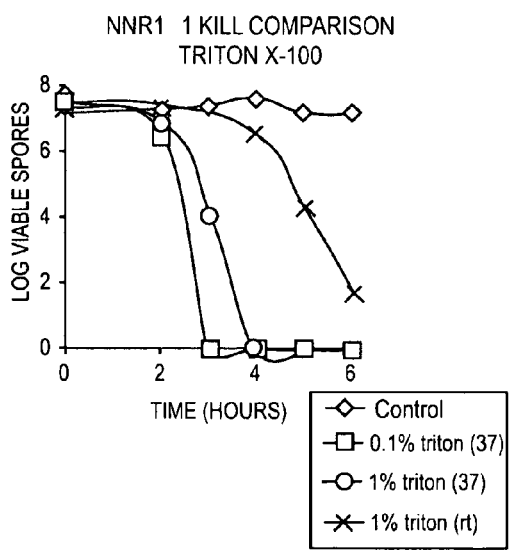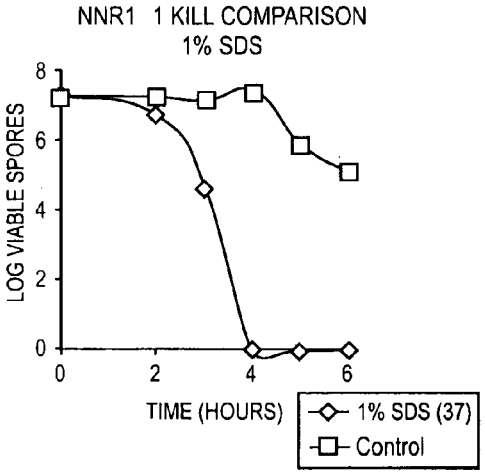

EFFECT OF ZWITTERION ON SPORE VIABILITY

EFFECT OF 3% ZWITTERION ON SPORE VIABILITY

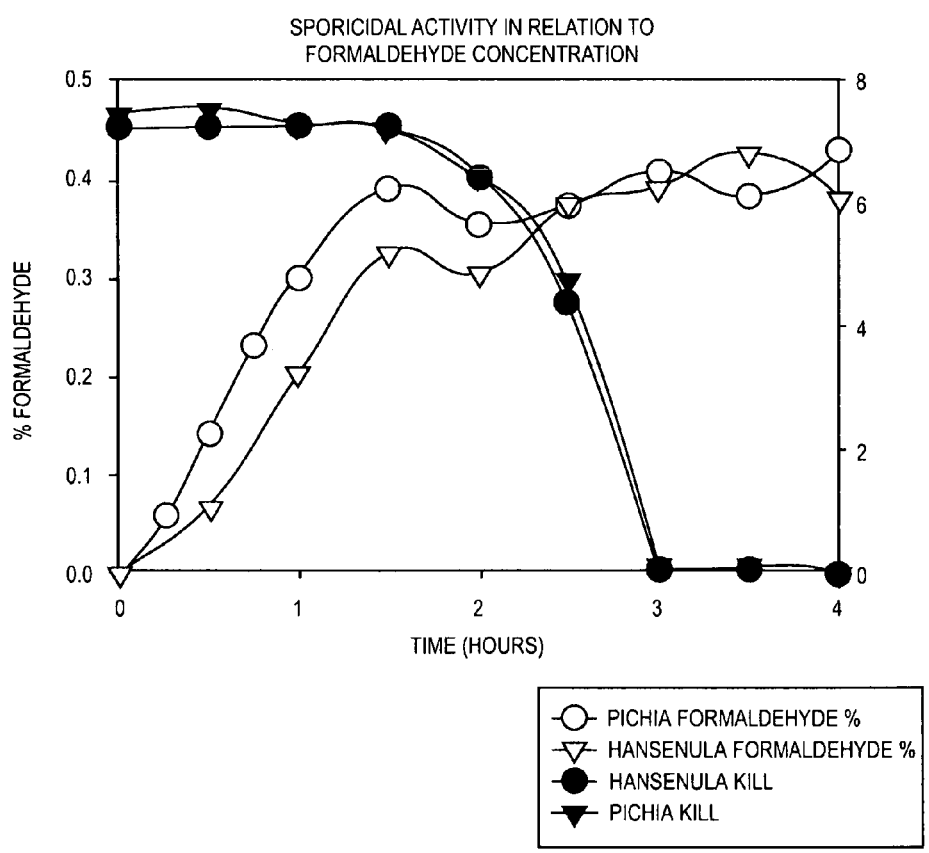

Fig. 10a

VEGETATIVE NNR1 CELL KILL

- ◇ CONTROL
- □ MeOH
- △ ETOH
- ○ MeOH + ALCOHOL OXIDASE
- × EtOH + ALCOHOL OXIDASE

X-axis: TIME (HOURS)
Y-axis: LOG (VIABLE CELLS)

Fig. 10b

YERSINIA PESTIS (A1122) CELL KILL

- ◇ CONTROL
- □ 20% METHANOL
- △ 20% METHANOL + PICHIA ALCOHOL OXIDASE

X-axis: TIME (HOURS)
Y-axis: LOG (VIABLE CELLS)

ENZYMATIC DECONTAMINATION

RELATED APPLICATION

This application claims the benefit of priority from U.S. provisional patent application Ser. No. 60/668,259 filed on Apr. 5, 2005.

GOVERNMENTAL INTEREST

The invention described herein may be manufactured, used and licensed by or for the U.S. Government.

TECHNICAL FIELD

This invention relates to materials and methods involved in enzymatic decontamination of hazardous materials.

BACKGROUND

Hazardous agents encompass a wide range of microbes and microbially derived compounds as well as other chemical compounds, including synthetic chemical compounds used in agricultural, military and industrial applications. Hazardous agents, including hazards of biological origin, for example, bacteria, bacterial endospores, viruses, viroids, fungi, protozoa and compounds produced by these organisms, and hazards derived from synthetic chemicals are of particular concern because of their potential for use as weapons of bioterrorism. In light of the serious health risks posed by hazardous agents, it is critical to be able to decontaminate surfaces or substances contaminated with these agents.

Decontamination of surfaces and substances contaminated with hazardous compounds can be carried out by chemical and enzymatic methods. Chemical based decontamination solutions such as DS2, although they are effective against both microbial and chemical agents, have toxic and corrosive properties. Enzymatic techniques are distinguished by low toxicities, making them relatively non-hazardous to personnel, equipment and the environment.

Enzymes are remarkable both for their catalytic power and exquisite substrate specificity. Enzymatic decontamination methods rely upon the ability of enzymes to catalyze the decomposition of their corresponding substrates. The catalytic power of enzymes allows them to detoxify many times their own weight in substrate in a short period of time. The substrate specificity of enzymes may restrict the applicability of any given enzyme to a particular molecular substrate or class of molecular substrate.

SUMMARY

Provided herein are methods for decontamination by inactivation of a hazardous agent comprising contacting the hazardous agent with a reactant mixture including an oxidoreductase enzyme that uses oxygen as an acceptor, an alcohol substrate, and a buffered medium suitable for maintaining enzymatic activity of the oxidoreductase enzyme that uses oxygen as an acceptor, under conditions such that the hazardous agent is rendered non-hazardous.

The hazardous agent can be a biological agent. The biological agent can be at least one agent selected from the group consisting of bacterial spores, vegetative bacteria, viruses, viroids, fungi, protozoa and toxins of biological origin. The bacterial spores can be from *Bacillus* species. The *Bacillus* species can be *Bacillus anthracis*. The vegetative bacteria can be from *Bacillus* species. The vegetative bacteria can be from *Yersinia* species.

In another embodiment, the hazardous agent can be a chemical agent. The chemical agent can be at least one agent selected from the group consisting of G-type chemical agents, V-type chemical agents, mustard agents, organophosphorus pesticides, organochlorine based pesticides and chlorinated solvents.

The oxidoreductase enzyme can include at least one oxidoreductase enzyme selected from the group consisting of alcohol oxidase, methyl alcohol oxidase, glucose oxidase, oxalate oxidase and aryl alcohol oxidase. The alcohol substrate can be a primary alcohol.

In another aspect, the reactant mixture can include a surfactant. The surfactant can include at least one surfactant selected from the group consisting of a non-ionic detergent, a cationic detergent, an anionic detergent and a zwitterionic detergent.

Implementations may include one or more of the following features. For example, the reactant mixture may include an acetyl donating compound. The reactant mixture may also include an organic carboxylic acid. The reactant mixture may also include a base catalyst.

In another embodiment, the reactant mixture includes at least one biodegradable and water soluble material selected from the group consisting of foams, wetting agents and degreasers prior to the contacting step. The reactant mixture can be contacted with the hazardous agent using a foam or spray system.

In a further embodiment, the reactant mixture can be combined with at least one enzyme selected from the group consisting of chitinase, laccase, organophosphorus hydrolase (OPH), organophosphorus acid anhydrolase (OPAA), *Loligo vulgaris* diisopropylfluorophosphatase (DFPase), lysozyme, mutanolysin, superoxide dismutase, and catalase. The reactant mixture may be combined with at least one enzyme selected from the group consisting of proteinases, amidases and peroxidases.

In another aspect, this document features a composition for decontamination by inactivation of a hazardous agent, the composition comprising an oxidoreductase enzyme that uses oxygen as an acceptor, an alcohol substrate, a buffered medium suitable for maintaining enzymatic activity of said oxidoreductase enzyme that uses oxygen as an acceptor and one reagent selected from the group consisting of an acetyl donor, an organic carboxylic acid, and a base catalyst.

Implementations may include one or more of the following features. The hazardous agent can be at least one biological agent as described above. The hazardous agent can be at least one chemical agent as described above. The oxidoreductase enzyme can include at least one oxidoreductase enzyme selected from the group consisting of alcohol oxidase, methyl alcohol oxidase, glucose oxidase, oxalate oxidase and aryl alcohol oxidase. The alcohol substrate can be a primary alcohol.

In another aspect, the composition can include at least one surfactant. The surfactant can include at least one surfactant selected from the group consisting of a non-ionic detergent, a cationic detergent, an anionic detergent and a zwitterionic detergent. The composition can include at least one biodegradable and water soluble material selected from the group consisting of foams, wetting agents and degreasers prior to the contacting step.

In another embodiment, this document provides a kit comprising packaging material and measured amounts of an oxidoreductase enzyme that uses oxygen as an acceptor, an alcohol substrate, a buffered medium suitable for maintaining enzymatic activity of said oxidoreductase enzymes that use oxygen as an acceptor, and at least one reagent selected from the group consisting of an acetyl donor, an organic carboxylic acid, and a base catalyst The kit may also include at least one enzyme selected from the group consisting of chitinase, laccase, organophosphorus hydrolase (OPH), organophosphorus acid anhydrolase (OPAA), *Loligo vulgaris* diisopropylfluorophosphatase (DFPase), lysozyme, mutanolysin, superoxide dismutase, and catalase. In another aspect, the kit can include at least one surfactant. The surfactant can include at least one surfactant selected from a group consisting of a non-ionic detergent, a cationic detergent, an anionic detergent and a zwitterionic detergent.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 3*a*, 3*b*, 3*c* and 3*d* are graphs plotting the sporicidal activity of alcohol oxidase in the presence of non-ionic, cationic and anionic surfactants.

FIG. 9 is a graph plotting the sporicidal activity of alcohol oxidases in relation to formaldehyde accumulation.

FIGS. 10*a* and 10*b* are graphs plotting the bacteriocidal activity of alcohol oxidase.

Like reference symbols in the various drawings indicate like elements.

DETAILED DESCRIPTION

Figure 1:
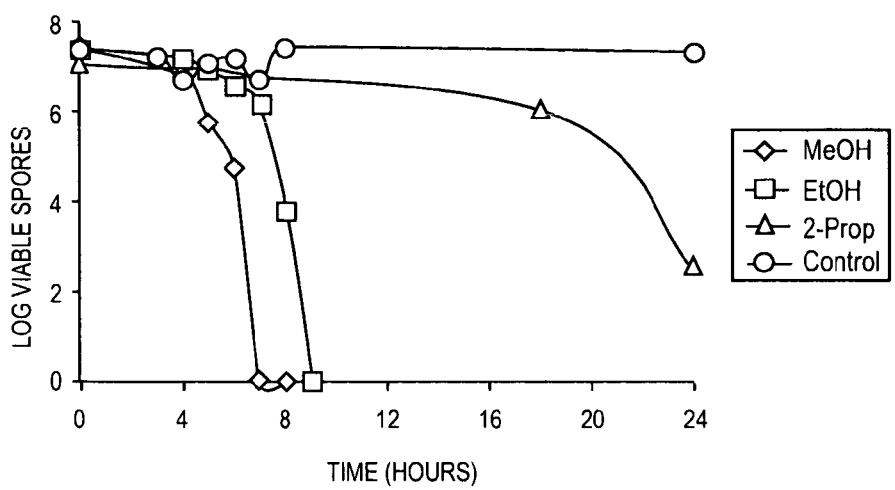
FIG. 1 is a graph plotting the sporicidal activity of alcohol oxidase in the presence of different alcohol substrates.

Hazardous agents of both microbial and chemical origin can be neutralized by hydrogen peroxide ($H_2O_2$). The materials and methods described here provide a method for enzymatic production of $H_2O_2$ in situ using oxidoreductase enzymes that use oxygen as an acceptor and their alcohol substrates.

Oxidoreductase enzymes that use oxygen as an acceptor, for example, alcohol oxidases, catalyze the oxidation of primary alcohols to generate the corresponding aldehyde and hydrogen peroxide. The enzymatically produced $H_2O_2$ and the corresponding aldehydes have potent bacteriocidal and sporicidal properties. The enzymatically produced $H_2O_2$ also provides a basis for the generation of compounds that can neutralize chemical agents. The decontaminating power of oxidoreductase enzymes that use oxygen as an acceptor can be amplified by the addition of other compounds that react with the enzymatically generated $H_2O_2$. For example, the addition of an acetyl donor such as acetylsalicylic acid, can produce peracetic acid, a very effective bactericidal, sporicidal and fungicidal agent. The addition of acetyl donating compounds or base catalysts can also generate reactive species that can neutralize chemical agents such as HD (mustard-type agents), V-type and G-type agents.

By using oxidoreductase enzymes that use oxygen as an acceptor and a combination of reagents, it is possible to neutralize both biological and chemical agents simultaneously. The catalytic production of aldehydes and peroxide in situ provides for the controlled synthesis of neutralizing agents in situ at their point of use and mitigates the need to store, transport and dispose of $H_2O_2$ solutions in the field. Thus, in one aspect this document features methods for using oxidoreductase enzymes that use oxygen as an acceptor for in situ generation of activity that neutralizes biohazardous agents. In another aspect, this document features materials and methods for the in situ detoxification of chemical agents.

I. Enzymes

Oxidoreductase enzymes that use oxygen as an acceptor can be employed to effect decontamination of hazardous agents. The term "enzyme" as used in this document refers to a protein that catalyzes at least one biochemical reaction. A compound for which a particular enzyme catalyzes a reaction is referred to as a "substrate" of the enzyme. An enzyme can be monomeric, comprising a single polypeptide chain of amino acids or multimeric, comprising one or more monomeric polypeptides, different or identical, that act together as a unit. Enzymes may also include cofactors, such as small molecules e.g., flavin adenine dinucleotide, or metal ions, that are required for enzymatic activity.

Enzymes are classified based upon the type of reaction they catalyze. The oxido-reductases, designated EC 1 (Enzyme Class 1), catalyze reduction/oxidation reactions or redox reactions. Redox reactions involve the transfer of electrons from one molecule (the oxidant or electron donor) to another (the reductant or electron acceptor) according to the scheme below.

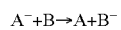

$A^- + B \rightarrow A + B^-$

As described herein, an oxidoreductase that uses oxygen as an acceptor is any enzyme that acts upon an alcohol substrate and uses $O_2$ as an electron acceptor to generate $H_2O_2$. Oxidoreductases are typically classified as EC1 by the nomenclature committee of the International Union of Biochemistry and Molecular Biology. Such oxidoreductases that use oxygen as an electron acceptor and alcohol as a substrate are generally found in the EC1.X.3.X class, where X can be any number, for example, alcohol oxidase (E.C.1.1.3.13), glucose oxidase (1.1.3.4), oxalate oxidase (1.2.3.4), and laccase (1.10.3.2) and aryl alcohol oxidase. In some embodiments, one or more different oxidoreductase enzymes and their corresponding substrates can be combined.

Oxidoreductase enzymes that use oxygen as an acceptor may be obtained from any organism. For example, enzymes can be obtained from bacterial, fungal, plant or animal sources. In some embodiments, methyl alcohol oxidases can be obtained from the yeasts, for example, *Pichia pastoris* or *Hansenula* spp. Oxidoreductase enzymes may be derived from crude cellular extracts or may be substantially purified. The term "substantially pure" with respect to a naturally-occurring enzyme refers to an enzyme that has been separated from cellular components by which it is naturally accompanied, such that it is at least 60% (e.g., 70%, 80%, 90%, 95%, or 99%), by weight, free from polypeptides and naturally-occurring organic molecules with which it is naturally associated. In general, a substantially pure polypeptide will yield a single major band on a non-reducing polyacrylamide gel.

A substantially pure polypeptide provided herein can be obtained by, for example, extraction from a natural source (e.g., a microorganism or plant), chemical synthesis, or by recombinant production in a host cell. Oxidoreductase polypeptides can be purified by any standard methods of protein purification, for example chromatographic methods including affinity chromatography, ion exchange chromatography, and gel filtration chromatography. See, for example, Caine et al., Protein Expr. Purif. (1996) 8(2):159-166. In addition, immunoaffinity chromatography can be used to purify oxidoreductase polypeptides.

The extent of purification can be measured using any appropriate method, including, without limitation, column chromatography, polyacrylamide gel electrophoresis, or high-performance liquid chromatography. Purification may also be monitored by assaying enzyme activity. Any standard method for assaying oxidoreductase activity may be used. For example, methyl alcohol oxidase activity can be assayed spectrophotometrically using dyes that react with $H_2O_2$ produced by methanol oxidation. Protein concentration can be determined by any standard method.

Recombinant oxidoreductase polypeptides also can be "engineered" to contain a tag sequence, such as green fluorescent protein (GFP), glutathione S-transferase (GST), six histidine (His6), c-myc, hemagglutinin, or Flag™ tag (Kodak) that allows the polypeptide to be purified (e.g., captured onto an affinity matrix). Tag sequences are typically expressed as a fusion with the polypeptide encoded by the nucleic acid sequence. Such tags can be inserted in a nucleic acid sequence such that they are expressed anywhere along an encoded polypeptide including, for example, at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEM (Promega, Madison, Wis.). Additionally, representative prokaryotic expression vectors include, without limitation, pBAD (Invitrogen, Carlsbad, Calif.), the pTYB family of vectors (New England Biolabs), and pGEMEX vectors (Promega); representative mammalian expression vectors include, without limitation, pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include, without limitation, pBacPAK8 or pBacPAK9 (Clontech), and p2Bac (Invitrogen); and representative yeast expression vectors include, without limitation, MATCHMAKER (Clontech) and pPICZ A, B, and C (Invitrogen).

For example, to produce a recombinant oxidoreductase polypeptide, a nucleic acid encoding an oxidoreductase polypeptide can be ligated into an expression vector and used to transform a prokaryotic (e.g., bacteria) or eukaryotic (e.g., insect, yeast, or mammal) host cell. In general, nucleic acid constructs can include a regulatory sequence operably linked to a nucleic acid encoding an oxidoreductase polypeptide. Regulatory sequences (e.g., promoters, enhancers, polyadenylation signals, or terminators) do not typically encode a gene product, but instead affect the expression of a nucleic acid sequence.

Recombinant oxidoreductase enzymes that use oxygen as an acceptor can also provide a basis for the production of mutant versions of the enzymes, that have additional properties and activities not found in the wild type enzymes. Mutant enzymes can be generated by any standard methods of in vitro mutagenesis, such as random mutagenesis or site directed mutagenesis, or by in vivo methods that involve subjecting host organisms to selection via nutritional or environmental stress.

Any molecular substrate that can undergo oxidoreductase catalyzed reduction/oxidation to yield $H_2O_2$ may be used. The substrate can be any aliphatic primary alcohol, for example, methanol, ethanol or 2-propanol, an aromatic alcohol, for example (2-naphthyl)methanol and 3-methoxybenzyl alcohol or a monosaccharide, for example D-glucose. In some embodiments, an aliphatic primary alcohol can include another organic functionality.

In some embodiments, enzymatic decontamination with oxidoreductase enzymes that use oxygen as an acceptor can include the addition of a surfactant. For example, some hazardous agents, e.g., *Bacillus* spores, contain numerous coats or layers that may impede entry of hydrogen peroxide and formaldehyde into the spore core, so that the addition of a surfactant to solubilize some of the outer layers can increase the efficiency of enzymatic decontamination. The term "surfactant", as used in this document, refers to a surface active agent that reduces the surface tension of the liquid in which it is dissolved. Surfactants are compounds that are amphipathic, that is, they contain both hydrophobic groups (the "tail") and hydrophilic groups (the "head"). Surfactants are classified based upon the presence or absence of charged groups in the head portion of the molecule. Non-ionic surfactants have no charged groups and can include, for example, alkyl polyglucosides, octyl phenol ethoxylate (triton-x-100) or poly(oxyethylene)(20)-sorbitane monooleate (tween 80). Anionic surfactants have a net negative charge and can include, for example, alkyl sulfate salts such as sodium dodecyl sulfate (SDS). Cationic surfactants have a net positive charge and can include alkyltrimethyl ammonium salts such as cetyl trimethyl ammonium bromide (CTAB). Zwitterionic surfactants contain a head with two oppositely charged groups and can include, for example, 3-(dodecyldimethylamino) propane sulfonate, dodecyl betaine, or dodecyl dimethylamine oxide. A single surfactant can be used or members from different classes of surfactants can be combined.

II Hazardous Agents

Hazards of biological origin. One suitable application of the enzymes discussed herein is for the in situ production of reagents with biocidal properties that can be used against a range of biological hazards. Biological hazards derive from pathogenic microorganisms including bacteria, bacterial spores, viruses, viroids, fungi, protozoa, and toxins of biological origin. Any biological hazard that is susceptible to attack by aldehydes and/or $H_2O_2$ may be targeted by the materials and methods provided herein.

The term "vegetative" bacteria as used herein refers to growing forms of pathogenic organisms, as opposed to the corresponding endospores. For example, bacterial pathogens can include, but are not limited to, *Bacillus anthracis, Yersinia*

*pestis, Clostridium botulinum, Francisella tularensis, Brucella* species, and *Staphylococcus aureus*.

The decontamination method described herein can also be used to kill bacterial endospores. Bacterial endospores, are metabolically inactive forms of bacteria that are resistant to inactivation by heat, drought, ultraviolet radiation, gamma irradiation, and many disinfectants. Endospores are produced by some gram positive bacteria, including, for example, the genera *Bacillus* and *Clostridium*. Endospores are readily aerosolized and once dispersed, can persist in the environment for periods of many years. Endospores from *Bacillus anthracis* are the causative agent of inhaled anthrax, a disease which is nearly always fatal.

The methods and compositions described herein can be used to neutralize contamination by agents of viral, viroidal, fungal or protozoal origin. For example, viral pathogens can include, without limitation, Hepatitis A, Arenaviruses, Bunyaviruses, Flaviviruses, Filoviruses, and viral encephalitides, such as West Nile virus. Viroidal pathogens can include members of the families Avsunviroidae and Pospiviroidae. Fungal pathogens can include, without limitation, members of the genera *Aspergillus, Penecillium, Stachybotrys*, and *Trichoderma*. Pathogenic protozoa can include, for example, members of the genera *Cryptosporidium, Giardia, Microsporidia* and *Toxoplasma*.

In another embodiment, the methods and compositions described herein can be used to neutralize biological toxins, e.g. toxic molecules produced by living organisms. Examples of biological toxins include, without limitation, ricin toxin from *Ricinus communis, Staphylococcus* enterotoxin B, and *Clostridium perfringens* epsilon toxin. Hazardous molecules of biological origin can also include prions and prion-like proteins e.g., the bovine spongiform encephalopathy (BSE) prion or variant, BovPrP$^{sc}$, or the Creutzfeldt-Jakob disease (CDJ) prion, HuPrP$^{sc}$.

The World Health Organization Guidelines on Blood Safety and Clinical Technology (information available on the WHO website at www.who.int) define sterilization as "the destruction or removal (by filtration) of all microorganisms and spores". Microorganisms are rendered non-hazardous by sterilization. Any standard assay method may be used to determine if sterilization of a surface or substance was successful. These assays can include techniques that directly measure microbial growth, e.g., the culture of swab samples or air samples on artificial growth media or spore outgrowth and viability assays. Other molecular detection methods, such as quantitative PCR, immunoassays such as ELISA or fluorescence activated cell sorting assays are also applicable.

Chemical hazards. The materials and methods described in this document can be used to detoxify G-type nerve agents developed for chemical warfare such as Sarin (GB; o-isopropyl methylphosphonofluoridate); Soman (GD; o-pinacolyl methylphosphonofluoridate); GF (o-cyclohexyl methylphosphonofluoridate); VX (S-2(diisopropyl)ethyl o-ethyl monophosphothioate); and tabun (GA; N,N-dimethylethyl phosphoroamidocyanidate) and the nerve agent analogue, DFP (diisopropyl fluorophosphate.) In another embodiment, oxidoreductase enzymes that use oxygen as an acceptor can be used to effect enzymatic hydrolysis of organophosphorus pesticides such as parathione and paraoxon, organochlorine-based pesticides and chlorinated solvents.

Addition of Acetyl Donors and Base Catalysts

The potency of oxidoreductase-mediated decontamination can be amplified by the addition of reagents that react with the enzymatically generated $H_2O_2$ to produce compounds that can neutralize biological and chemical hazards. For example, the addition of compounds containing acetyl groups, such as acetylsalicylic acid, to the base alcohol oxidase and non-ionic surfactant composition will react with the $H_2O_2$ generated in situ, to produce peracetic acid, a molecule with potent bacteriocidal, sporicidal and fungicidal properties, in situ. Other acetyl donors may include, for example, acetic acid. The in-situ formed peracetic acid can also act to detoxify chemical agents. Sulfur or mustard-type agents for example, 2-2'-Dichlorodiethylsulfide (sulfur mustard) can be readily oxidized to sulfoxide and sulfone analogs. The peroxyacid will neutralize VX through oxidation of the thiol-sulfur followed by hydrolysis.

The addition of base catalysts to the in situ generated $H_2O_2$ can also be used to detoxify chemical agents. In the presence of base, such as sodium carbonate, sodium bicarbonate or molybdates, $H_2O_2$ yields the hydroperoxy anion, HOO—. This anion is a very powerful nucleophile which neutralizes V-type and G-type chemical agents by an SN2 mechanism. The major products are the corresponding alkyl methylphosphonic acids. Both the peroxyacid and hydroperoxy anion resulting from interaction with in-situ formed $H_2O_2$ will also display strong biocidal properties.

III. Decontamination

Decontamination as used herein is the process of neutralizing, destroying or removing hazardous agents from a person, object or space, thereby rendering them safe. Oxidoreductases that use oxygen as an acceptor may be used to effect decontamination of surfaces or substances that are contaminated with hazardous compounds, including but not limited to buildings and their contents, vehicles, military equipment, medical equipment, tools, transportation systems, water supplies and infrastructure, community infrastructure, the natural environment including soil, plants and bodies of water, personnel and animals. Contaminated surfaces or substances may result from any number of causes, including but not limited to, chemical warfare attacks, military operations, chemical manufacturing, scientific research, agricultural application of pesticides, toxic waste storage, and accidental spills occurring during the use of any hazardous compound.

The composition comprising an oxidoreductase enzyme that uses oxygen as an acceptor, substrates, surfactants and additional reagents for generating HOO— may be applied to contaminated surfaces or substances in any formulation suitable for decontamination. The formulation may include, but is not limited to, biodegradable water soluble materials such as foams, wetting agents or degreasers, for example, AFC-380®, BioSolve®, Cold FireRetardant®, Cold Fire®, BV 406LF®, and Odor Seal®. The material may also be prepared in any formulation suitable for use in humans or animals. The enzymatic decontamination reagents supplied herein also may be lyophilized, using any standard method of lyophilization, for long term storage and then reconstituted at their point of use. A lyophilized composition may include reagents that aid in stability of enzymes during the lyophilization and reconstitution process. Such reagents may include, but are not limited to, trehalose, glycerol, sucrose, and $MnCl_2$.

Oxidoreductases that use oxygen as an acceptor and the related methods provided in this document may also be used to detoxify stocks of hazardous compounds. Stocks of hazardous compounds may include, but are not limited to chemical or biological warfare agents, pesticides, chlorinated solvents, and toxic wastes.

In another embodiment, the material and methods provided in this document for oxidoreductase-mediated decontamination may be combined with other enzymes that neutralize biological or chemical agents. Enzymes with antimicrobial activity include, without limitations, chitinase, lysozyme, and mutanolysin; enzymes that hydrolyze chemical agents include, without limitation, organophosphorus hydrolase (OPH), organophosphorus acid anhydrolase (OPAA), and *Loligo vulgaris* diisopropylfluorophosphatase (DFPase). The activity of the oxidoreductase enzymes may also be modulated by the addition of catalase, super oxide dismutase, proteinases, amylases and peroxides.

The reagents used for enzymatic decontamination can be combined as an article of manufacture, for example, as a kit. A kit may include an oxidoreductase enzyme that uses oxygen as an acceptor, an alcohol substrate for the enzyme, a surfactant, chemical buffers and reagents such as acetyl donating compounds or base catalysts for the production of compounds that neutralize chemical agents. Such kits may also include reagents that promote the stability of the enzymes. The reagents within a kit can be housed together in various combinations or can be packaged in separate vials or containers. The kits provided herein can also include labels or packaging inserts setting out instructions for preparation and use.

EXAMPLES

Example 1

Effect of Alcohol Substrate on Sporicidal Activity Mediated by Alcohol Oxidase Catalyzed Oxidation Materials and Methods

*Bacillus anthracis* NNR1Δ1 (strain) spores were produced in accordance with the protocol described by Dang, et al. (Applied and Environmental Microbiology (2001) 67: 3665-3670). Spore viability was challenged using alcohol oxidase to break down alcohol into peroxide and the corresponding aldehyde (e.g. methanol is converted to hydrogen peroxide and formaldehyde). Alcohol Oxidase (EC: 1.1.3.13) from *Pichia pastoris* was purchased from Sigma-Aldrich (catalogue number A2404). Approximately $2 \times 10^7$ spores were added to an assay buffer containing 20% alcohol, 0.1% tween-80, 100 mM potassium phosphate buffer, pH 7.4, and 20 units of alcohol oxidase in a total volume of 1 mL. Control samples, in which the alcohol oxidase was omitted, included 20% methanol, 0.1% tween-80, and 100 mM potassium phosphate buffer, pH 7.4. Mixtures were vigorously shaken at 200 rpm over the duration of the exposure. At specified times, 100 µL of each sample was removed and mixed with 900 µL of sterile distilled water. These samples were centrifuged for 8 minutes at 10,000×g to pellet the spores. The supernatant was removed and the spores resuspended in 1 mL of sterile distilled water. The centrifugation step was repeated two more times to remove any remaining substrate, enzyme, or enzyme reaction products.

For spore outgrowth and viability measurements, serial dilutions of each sample were created using sterile distilled water. 100 microliters (µL) of each dilution were spread on Tryptic Soy Agar (TSA) plates in duplicate. Plates were incubated at 37° C. overnight to allow outgrowth of viable spores. Colonies were counted using a QCount® (Spiral Biotech).

The efficiency of *Bacillus anthracis* NNR1Δ1 spore kill in the presence of alcohol oxidase catalyzed oxidation of three different alcohol substrates, methanol (MeOH), ethanol (ETOH), and 2-propanol (2-Prop), was compared. The results, shown in FIG. 1, indicated that spore kill efficiency was substrate-dependent. The products of methanol oxidation killed spores within an eight hour time period at 27° C. Ethanol oxidation produced a total kill in 10 hours while 2-propanol was unable to produce a total kill over 24 hr.

Example 2

Effect of Methanol Concentration on Sporicidal Activity Mediated by Alcohol Oxidase Catalyzed Oxidation Under Environmental Protection Agency/Department of Transportation regulations, methanol at concentrations below 10% is not considered to be a hazardous material for transport purposes. Therefore, the efficiency of *Bacillus anthracis* NNR1Δ1 spore kill in the presence of alcohol oxidase catalyzed oxidation at a 10% methanol (MeOH) concentration was evaluated. Triplicate spore samples were assayed for viability in the presence of 20 units of *Pichia pastoris* alcohol oxidase and 10% methanol. Spore viability assay conditions were as described in Example 1 except that the assay buffer contained 0.1% triton-X-100 and 100 mM potassium phosphate. Control samples, from which alcohol oxidase was omitted, included 10% methanol, 0.1% triton-X-100 and 100 mM potassium phosphate. Spore outgrowth and viability measurements were performed according to the methods in Example 1.

Figure 2:
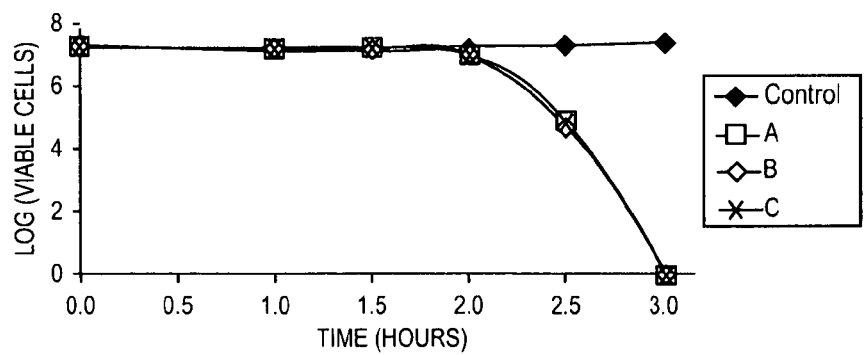
FIG. 2 is a graph plotting the sporicidal activity of alcohol oxidase in the presence of 10% methanol.

The results, shown in FIG. 2, indicated a 10% methanol concentration was effective in supporting alcohol oxidase-mediated spore kill. The triplicate samples (curves A, B and C in FIG. 2) all showed a rate of spore kill, 100% within 3 hours, that was very similar to the rate obtained with a 20% methanol concentration.

Example 3

Effect of Temperature on Sporicidal Activity Mediated by Alcohol Oxidase Catalyzed Oxidation The efficiency of *Bacillus anthracis* NNR1Δ1 spore kill in the presence of alcohol oxidase catalyzed oxidation at 37° C. was evaluated. Spore viability assays included 20 units of *Pichia pastoris* alcohol oxidase, 20% methanol, 0.1% Tween-80 and 100 mM potassium phosphate. Spore outgrowth and viability assays were carried out as described in Example 1. Increasing the reaction temperature from 27° C. to 37° C. decreased the time required for a complete kill from 8 hours to 5 hours.

Example 4

Effect of Surfactant on Sporicidal Activity Mediated by Alcohol Oxidase Catalyzed Oxidation

*Bacillus* spores contain numerous coats or layers that may impede entry of hydrogen peroxide and formaldehyde into the spore core; addition of a surfactant to solubilize some of the outer layers and increase the efficiency of killing of *Bacillus anthracis* NNR1Δ1 spores was explored. Representatives of four classes of surfactants, non-ionic (triton-X-100, tween-80), cationic (cetyltrimethylammonium bromide (CTAB), anionic (sodium dodecyl sulfate (SDS), and zwitterionic (3-(dodecyldimethylamino) propane sulfonate) were chosen for further analysis.

Figure 4A:
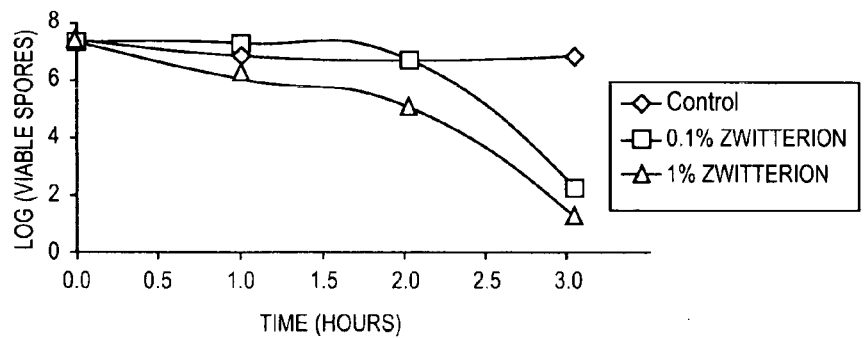
FIGS. 4*a* and 4*b* are graphs plotting the sporicidal activity of alcohol oxidase in the presence of a zwitterionic surfactant.
Figure 4B:
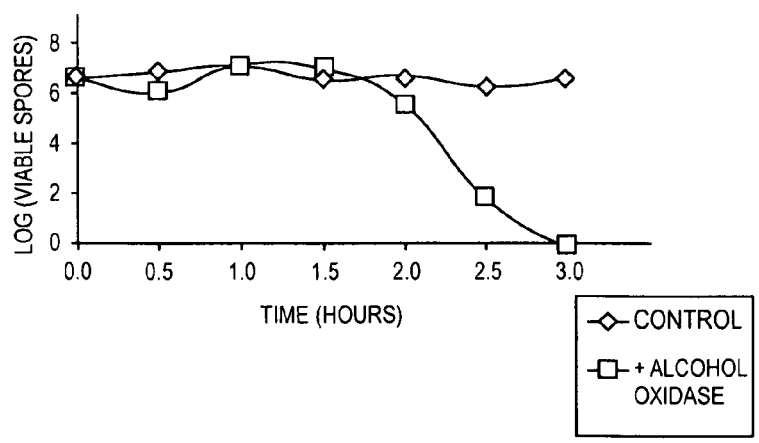

The non-ionic, cationic and anionic surfactants were evaluated in spore viability assays that included 20 units of *Pichia pastoris* alcohol oxidase, 20% methanol, and 100 mM potassium phosphate. Surfactants were tested at 1% and 0.1% (v/v) and at both 27° C. (RT) and 37° C. (37). Control samples for all the surfactant experiments (as shown in FIGS. 3 and 4) contained surfactant as indicated in the Figure legends, 20% methanol, 100 mM potassium phosphate, but did not include the alcohol oxidase. The results shown in FIGS. 3a, 3b, 3c and 3d indicated that the non-ionic surfactants were more effective at increasing spore kill efficiency than were the anionic or cationic surfactants. Of the conditions tested in this experiment, the most efficient formulation for spore inactivation contained 0.1% triton X-100, 100 mM potassium phosphate (pH 7.4) and 20% methanol at 37° C.

The zwitterionic surfactant (3-(dodecyldimethylamino) propane sulfonate) was evaluated in spore viability assays as described above at concentrations of 0.1%, 1% and 3%. The results shown in FIGS. 4a and 4b indicated that highest concentration of zwitterionic surfactant (3%) was the most efficient at promoting spore killing.

Example 5

Effect of Combinations of Surfactants on Sporicidal Activity Mediated by Alcohol Oxidase Catalyzed Oxidation The data shown in Example 3 indicated that some surfactants were more potent than others in enhancing the rate of alcohol oxidase-mediated spore killing. Further experiments were performed to determine whether combinations of surfactants might provide additional enhancement in the rate of spore killing. Spore viability assays included 20 units of Pichia pastoris alcohol oxidase, 0.1% triton X-100, 100 mM potassium phosphate (pH 7.4), 20% methanol and either 1% or 3% zwitterionic surfactant (3-(dodecyldimethylamino) propane sulfonate) (ZI).

Figure 5A:
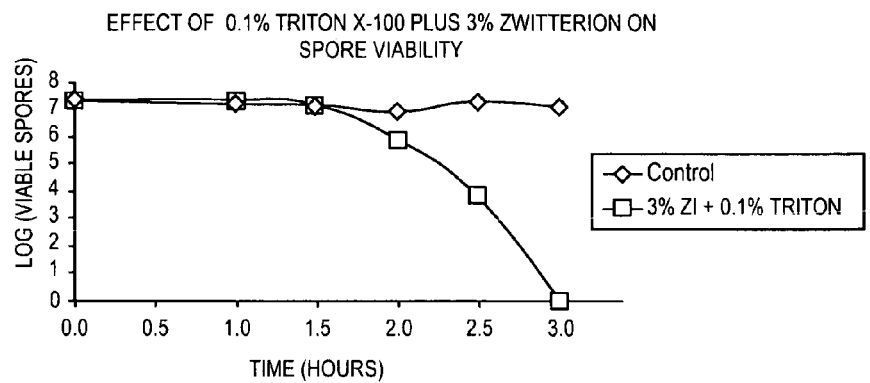
FIGS. 5*a* and 5*b* are graphs plotting the sporicidal activity of alcohol oxidase in the presence of a combination of surfactants.
Figure 5B:
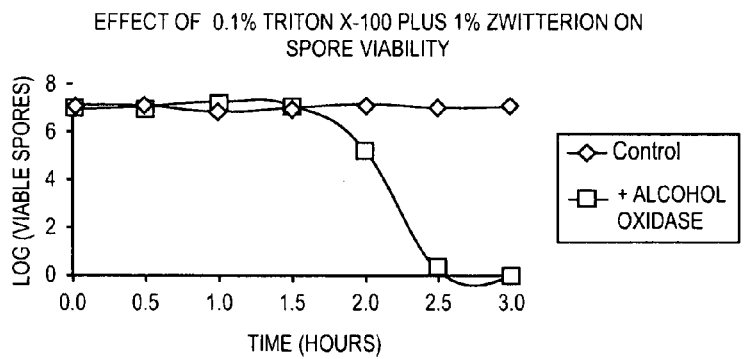

The data in FIG. 5 indicated that a combination of 0.1% triton-X-100 with 3% zwitterions had no effect on kill rate (FIG. 5a) relative to the kill rate achieved with 0.1% triton-X-100 alone (Compare FIG. 5a with FIG. 4c). However, as shown in FIG. 5b, the combination of 0.1% triton-X-100 with 1% zwitterion resulted in a 2-3 log greater kill at 2.5 hours than was observed with either of the surfactants alone.

Example 6

Figure 6:
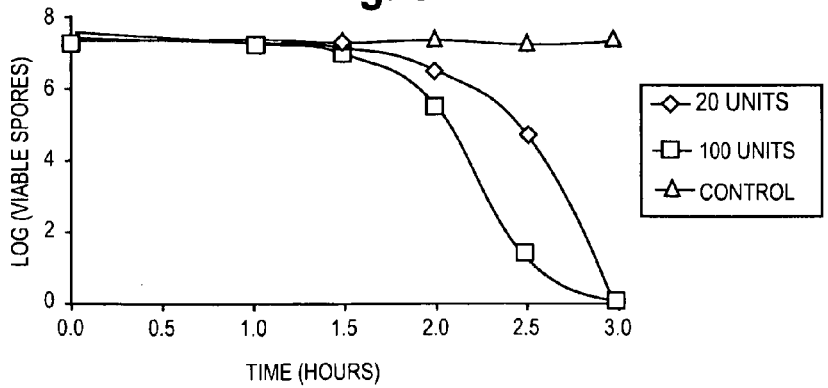
FIG. 6 is a graph plotting the sporicidal activity of alcohol oxidase as a function of enzyme concentration.

Effect of Alcohol Oxidase Concentration on Sporicidal Activity Mediated by Alcohol Oxidase Catalyzed Oxidation The efficiency of Bacillus anthracis NNR1Δ1 spore kill at two concentrations of alcohol oxidase was compared. Spore viability assays were performed at 37° C. as in Example 1; assays contained either 20 or 100 units of alcohol oxidase, 20% methanol, 0.1% triton-X-100 and 100 mM potassium phosphate (pH 7.4). Increased concentrations of enzyme resulted in a dose-dependent increase in the rate of sporicidal activity as shown in FIG. 6.

Example 7

Figure 7:
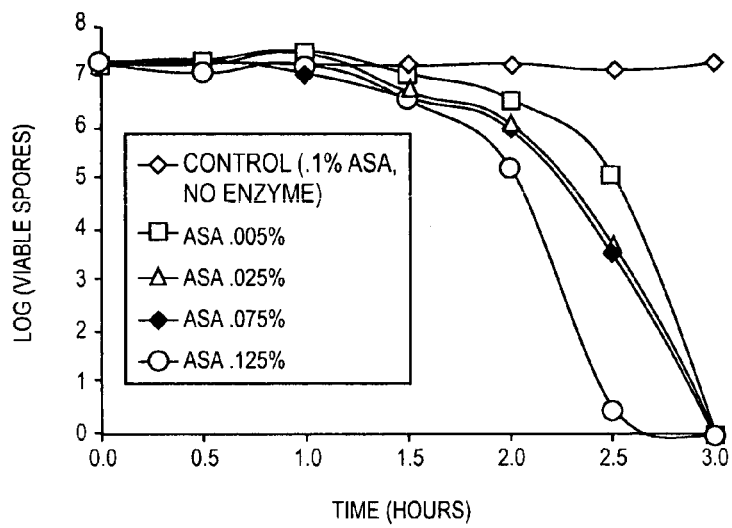
FIG. 7 is a graph plotting the sporicidal activity of alcohol oxidase as a function of acetylsalicylic acid concentration.

Effect of the Addition of Acetyl Donor Compounds on Sporicidal Activity Mediated by Alcohol Oxidase Catalyzed Oxidation The addition of compounds containing acetyl donor groups to the alcohol oxidase reaction, through reaction with the peroxide generated by the alcohol oxidase cleavage of the alcohol substrate, produces peracetic acid, a potent biocide. The efficiency of Bacillus anthracis NNR1Δ1 spore kill by alcohol oxidase catalyzed oxidation of methanol in the presence of different concentrations of the acetyl donating molecule, acetylsalicylic acid (ASA), was analyzed. Spore viability assay reactions contained 20 units of alcohol oxidase, 20% methanol, 0.1% trition-X-100, 100 mM potassium phosphate (pH 7.4) and either 0.005%, 0.025%, 0.75% or 0.125% acetylsalicylic acid. Control samples, in which the enzyme was omitted, contained 0.1% acetylsalicylic acid. The results shown in FIG. 7 indicated that increasing concentrations of acetylsalicylic acid resulted in increased efficiency of spore killing.

Figure 8:
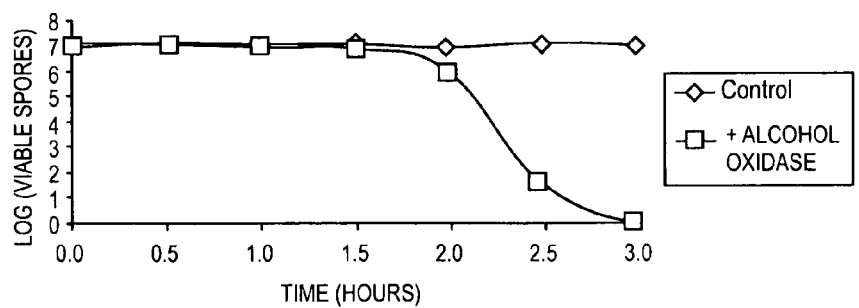
FIG. 8 is a graph plotting the sporicidal activity of alcohol oxidase in the presence of acetic acid.

Acetic acid was also evaluated for its ability to function as an acetyl donor compound. Assay conditions were identical to those described above for acetylsalicylic acid except that reactions contained 0.125% acetic acid instead of peracetic acid. Control samples, in which the enzyme was omitted, contained 0.125% acetic acid. Results of this experiment, shown in FIG. 8, indicated that 0.125% acetic acid enhanced the kill rate to about the same degree as did 0.125% acetylsalicylic acid.

Example 8

Comparative Analysis of Formaldehyde Production and Sporicidal Activity

Since many fungi utilize methanol as a carbon source, the relative efficiency of alcohol oxidase activity from Pichia pastoris was compared with that of another yeast species, Hansenula. Alcohol oxidase (EC: 1.1.3.13) from Hansenula sp. was purchased from Sigma-Aldrich (catalogue number A0438). Spore viability assays (performed at 37° C.) comparing enzymes from the two sources and containing 20 units of alcohol oxidase, 20% methanol, 0.1% trition-X-100, 100 mM potassium phosphate (pH 7.4) showed a nearly identical activity of 100% killing at 3 hours for both enzymes.

The relationship between sporicidal activity and formaldehyde production was then explored in a time course assay using alcohol oxidase from Pichia pastoris and Hansenula. Spore viability assay conditions were as described in Example 1. Formaldehyde concentration was determined using Nash reagent (30 g of ammonium acetate, 0.4 mL of acetyl acetone (2,4-pentandione), and 0.6 mL of glacial acetic acid in a total volume of 100 mL.) (Nash T: The calorimetric estimation of formaldehyde by means of the Hantzshi reaction. Biochem J 55:416-421, 1953). Nash reagent was added to the alcohol oxidase formulation at a 1:1 (v/v) and incubated at 50° C. for 20 min. Upon completion of incubation, the absorbance at 412 nm was taken. The concentration of formaldehyde in the alcohol oxidase reactions was calculated based upon a standard curve of known formaldehyde concentrations.

The results of this experiment, shown in FIG. 9, indicated that the maximum amount of formaldehyde produced in reactions containing 20% methanol was 0.45% (w/v). The maximum levels were achieved at about 1.5 hours of incubation. The corresponding spore kill curves indicated that the decrease in spore viability began once this maximum concentration was reached. The rates of both formaldehyde production and spore killing were very similar for both enzymes.

Example 9

Effect of Alcohol Oxidase on Spore Structure

Phase contrast microscopy was used to evaluate the effects of alcohol oxidase treatment on Bacillus anthracis NNR1Δ1 spore morphology. In particular, microscopic analysis was used to determine the point in the *B. anthracis* life cycle that the formulation exerted its sporicidal effects i.e. before or after spore germination. Spores were collected from control and alcohol oxidase-treated samples at intervals after alcohol oxidase treatment according to the method in Example 1. Ten μL of a spore sample was placed on a glass slide and dispersed under a glass cover slip. Samples were viewed using an Olympus BX50 microscope.

Phase contrast microscopy indicated that spores were clearly visible in both the alcohol oxidase treated sample and the controls even at 24 hours after treatment. However, the spores in the treated samples were incapable of outgrowth. These data showed that the formulation was indeed killing the spores, rather than inducing germination followed by kill of the germinated cells.

Example 10

Bacteriocidal Activity of Alcohol Oxidase

The alcohol oxidase formulations described above were also evaluated for bacteriocidal activity against *B. anthracis* vegetative cells, as well as against vegetative cells from another pathogen, *Yersinia pestis*. For the production of vegetative *B. anthracis* NNR1Δ1 cells, spores were streaked onto TSA plates and incubated overnight at 37° C. A single colony was selected, placed in Tryptic Soy Broth (TSB), and incubated overnight at 37° C. The saturated culture was back diluted in fresh TSB in the morning and grown to an OD600 of approximately 0.6 or mid-log phase. 400 μL of the mid-log phase culture was added to the alcohol oxidase formulation to test for efficacy. In the alcohol oxidase challenge, phosphate-buffered saline (PBS) was used in place of sterile distilled water.

*Yersinia pestis* strain A1122 was a gift of Dr. Laura Rose of the Center for Disease Control in Atlanta, Ga. For the production of vegetative *Yersinia pestis* strain A1122 cells, a single colony was suspended in 500 μl of BHI broth (Brain Heart Infusion). This was then spread onto TSA II (Tryptic Soy Agar supplemented with 5% sheep's blood). The culture was grown at 37° C. for 48 hr to form a confluent lawn. The lawn was suspended, using a spreader, in 2 mL PBS. The culture was then removed from the plate and placed into a sterile 1.5 mL eppendorf tube. The alcohol oxidase challenge was performed as described above except that 100 μL of the suspended culture was used for the initial challenge and PBS was used in place of sterile distilled water.

The bacteriocidal activity of the alcohol oxidase formulation against vegetative *B. anthracis* NNR1Δ1 cells and *Yersinia pestis* A1122 cells is shown in FIGS. 10a and 10b, respectively. Cell viability assays were performed at 37° C. Reactions included 20 units of alcohol oxidase, 20% methanol or ethanol (as indicated in FIG. 10a), 0.1% trition-X-100, 100 mM potassium phosphate (pH 7.4). The results indicated that the alcohol oxidase formulation was effective in killing vegetative bacterial cells. Furthermore, the temporal pattern of alcohol oxidase bacteriocidal activity was similar to the temporal pattern of alcohol oxidase sporicidal activity.

A number of embodiments of the invention have been described. Nevertheless, it will be understood that various modifications may be made without departing from the spirit and scope of the invention. Accordingly, other embodiments are within the scope of the following claims.

What is claimed is:

1. A method for decontamination of a hazardous agent, comprising: producing a reactant mixture by mixing an oxidoreductase enzyme that uses oxygen as an acceptor, an alcohol substrate comprising methanol for said oxidoreductase enzyme, and a buffered medium suitable for maintaining enzymatic activity of said oxidoreductase enzyme, under conditions which maintain the enzymatic activity of said oxidoreductase enzyme so that the oxidoreductase enzyme and the methanol substrate enzymatically produce two antimicrobials consisting of hydrogen peroxide and formaldehyde contacting said hazardous agent comprising a biological agent and/or a chemical agent with said reactant mixture so that said hazardous agent is rendered non-hazardous by said antimicrobials, and further adding an acetyl donating compound to said reactant mixture so that decontaminating power is amplified by the formation of peracetic acid thereby improving bactericidal, sporicidal and fungicidal properties of the reactant mixture.

2. The method of claim 1, wherein said acetyl donating compound is selected from the group consisting of acetylsalicyclic acid and acetic acid.

3. The method of claim 1, further comprising adding a base catalyst to said reactant mixture so that decontaminating power is amplified by the formation of hydroperoxy anion.

4. The method of claim 3, wherein said base catalyst is selected from the group consisting of sodium carbonate, sodium bicarbonate and molybdates.

5. The method of claim 1, wherein said hazardous agent is a biological agent.

6. The method of claim 5, wherein said biological agent is at least one agent selected from the group consisting of bacterial spores, vegetative bacteria, viruses, viroids, fungi, protozoa and toxins of biological origin.

7. The method of claim 6, wherein said bacterial spores are from *Bacillus* species.

8. The method of claim 7, wherein said *Bacillus* species is *Bacillus anthracis*.

9. The method of claim 6, wherein said vegetative bacteria are from *Bacillus* species.

10. The method of claim 6, wherein said vegetative bacteria are from *Yersinia* species.

11. The method of claim 1, wherein said hazardous agent is a chemical agent.

12. The method of claim 11, wherein said chemical agent is at least one agent selected from the group consisting of G-type chemical agents, V-type chemical agents, mustard agents, organophosphorus pesticides, organochlorine based pesticides and chlorinated solvents.

13. The method of claim 1, wherein said oxidoreductase enzyme comprises at least one oxidoreductase enzyme selected from the group consisting of alcohol oxidase, methyl alcohol oxidase, glucose oxidase, oxalate oxidase and aryl alcohol oxidase.

14. The method of claim 1, wherein said reactant mixture further comprises a surfactant.

15. The method of claim 14, wherein said surfactant comprises at least one surfactant selected from the group consisting of a non-ionic detergent, a cationic detergent, an anionic detergent and a zwitterionic detergent.

16. The method of claim 1, wherein said reactant mixture further comprises an organic carboxylic acid.

17. The method of claim 1, wherein said reactant mixture further comprises at least one biodegradable and water soluble material selected from the group consisting of foams, wetting agents, and degreasers prior to the said contacting step.

18. The method of claim 17, wherein said reactant mixture is contacted with said hazardous agent using a foam or spray system.

19. The method of claim 1, wherein said reactant mixture is combined with at least one enzyme selected from the group consisting of chitinase, laccase, organophosphorus hydrolase (OPH), organophosphorus acid anhydrolase (OPAA), *Loligo vulgaris* diisopropylfluorophosphatase (DFPase), lysozyme, mutanolysin, superoxide dismutase, and catalase.

20. The method of claim 1, wherein said reactant mixture is combined with at least one enzyme selected from the group consisting of proteinases, amidases and peroxidases.

21. The method of claim 1, wherein said conditions include a pH of about 7.4.

22. The method of claim 1, wherein said reactant mixture comprises about 20 units of said oxidoreductase enzyme per milliliter of solution and about 20% of said alcohol buffered to a pH of about 7.4.

* * * * *